United States Patent [19]

Roy et al.

[11] Patent Number: 5,266,717
[45] Date of Patent: *Nov. 30, 1993

[54] N-(SULFOMETHYL)-N'ARYLUREAS

[76] Inventors: Glenn Roy, 211 N. Oltendorf, Streamwood, Ill. 60107-1755; Chris Culberson, 229 S. Salem Dr., Schaumburg, Ill. 60193; George Muller, 1915 Smith Rd., Northbrook, Ill. 60062; Srinivasan Nagarajan, 700 W. Rand, πC205, Arlington Heights, Ill. 60004

[*] Notice: The portion of the term of this patent subsequent to Feb. 19, 2008 has been disclaimed.

[21] Appl. No.: 599,319

[22] Filed: Oct. 17, 1990

Related U.S. Application Data

[63] Continuation of Ser. No. 331,997, Apr. 3, 1989, Pat. No. 4,994,490.

[51] Int. Cl.$^5$ .................. C07C 255/42; C07C 309/56
[52] U.S. Cl. ...................... 558/413; 560/13; 562/44
[58] Field of Search .................. 562/44; 426/535, 548, 426/658; 558/413; 560/13

[56] References Cited

U.S. PATENT DOCUMENTS

| | | | |
|---|---|---|---|
| 2,785,195 | 3/1957 | Beck et al. | 426/548 X |
| 4,067,910 | 1/1978 | Frater et al. | 426/535 X |
| 4,544,565 | 10/1985 | Barnett | 426/538 |
| 4,642,240 | 2/1987 | Barnett et al. | 426/538 |
| 4,645,678 | 2/1987 | Nofre et al. | 426/548 |
| 4,673,582 | 6/1987 | Nofre et al. | 426/548 |

FOREIGN PATENT DOCUMENTS

| | | |
|---|---|---|
| 125049 | 11/1984 | European Pat. Off. |
| 159864 | 10/1985 | European Pat. Off. |
| 207515 | 1/1987 | European Pat. Off. |
| 2139470A | 11/1984 | United Kingdom |
| 2180534A | 4/1987 | United Kingdom |

OTHER PUBLICATIONS

Tinti, et al.; C.A. 98:15626f (1983), 78.
C.A., 11th Coll. Formula Index (1982–1986) p. 4390f.
Tinti, et al.; "Z Lebensm.–Unters. Forsch.", (1982), pp. 266–268.
C.A., vol. 43, 168 b to i (1949), Petersen, et al.

Primary Examiner—Joseph Paul Brust
Attorney, Agent, or Firm—Jeffery M. Hoster; John M. Sanders

[57] ABSTRACT

N-(sulfomethyl)-N'-arylureas inhibit or suppress bitter and sweet tastes when mixed with sweet and/or bitter tasting compositions, such as foods, beverages and pharmaceutical preparations.

4 Claims, No Drawings

N-(SULFOMETHYL)-N'ARYLUREAS

This is a continuation of application Ser. No. 331,997 filed Apr. 3, 1989 now U.S. Pat. No. 4,994,490 issued Feb. 19, 1991.

BACKGROUND OF INVENTION

The present invention relates to novel compounds which exhibit taste modifying properties. In particular, aminomethylsulfonic acid containing aryl ureas and physiologically acceptable salts thereof inhibit sweet and/or bitter tastes. The present invention also relates to compositions containing these novel compounds and to methods of inhibiting sweet and/or bitter tastes in foods, beverages and pharmaceuticals.

Sweetness inhibitors are known in the art and are useful in food products where sweetness intensity needs to be lessened. Sweetness inhibitors are known that inhibit the sweet taste of natural and high potency sweeteners including sugar, other carbohydrate sweeteners, sugar alcohols, high fructose corn syrup, proteins, dipeptides (aspartame, alitame), saccharin, acesulfam K (Ace-K) and trichlorogalactosucrose (TGS).

European Patent Application 86109045.4 (published Jan. 7, 1987 as publication number 0 207 515) discloses alkali metal and alkaline metal salts of heptyl sulfonate and octylsulfonate as sweetness inhibitors. UK Patent Application GB 2,139,470 A discloses aryl carboxylic acid salts as sweetness inhibitors of sugar or sugar alcohols. U.S. Pat. No. 4,544,565 discloses arylalkyl ketones as sweetness inhibitors. U.S. Pat. No. 4,642,240 discloses substituted benzoic acids, benzenesulfonic acids, benzenephosphoric acids and benzeneboronic acids as sweetness inhibitors. Uk Patent Application GB 2,180,534 A discloses benzoyloxyacetic acid derivatives useful as sweetness inhibitors. Ethers and thioethers of acetic derivatives are disclosed as taste modifiers and sweetness inhibitors of sugar and sugar alcohols in European Patent Application 85302546.8 (Publication No. 0 159 864 published Oct. 30, 1985). Likewise, the sweetness of sugars and sugar alcohols is inhibited by phenylalkanoic acid salts as disclosed in European Patent Application 84302496.9 (Publication No. 0 125 049 published Nov. 14, 1984).

Many of the known sweetness inhibitors have a bitter taste. The present aryl urea taste modifiers are tasteless at use levels and inhibit both sweet and organic, bitter tasting substances.

SUMMARY OF INVENTION

Briefly, in accordance with the present invention, N-(sulfomethyl)-N'-arylureas inhibit or suppress bitter and sweet tastes when added to sweet and/or bitter tasting compositions. The N-(sulfomethyl)-N'-arylureas (aryl ureas), are added to sweet and/or bitter tasting compositions in amounts of from about 0.01 to about 10 weight percent of the composition. Food, beverage or pharmaceutical compositions which are overly sweet and/or bitter can be made more palatable by the addition of the present aryl ureas.

Of particular interest, N-(sulfomethyl)-N'-(4-cyanophenyl)urea, N-(sulfomethyl)-N'-(4-carbamoylphenyl)urea, N-(sulfomethyl)-N'-(4-formylphenyl)urea and physiologically acceptable salts thereof are added to overly sweet and/or bitter foods, beverages or pharmaceuticals in order to make them more palatable.

DETAILED DESCRIPTION OF THE INVENTION

In practicing the present invention, the present aryl ureas are added to foods, beverages or drugs to inhibit or lessen sweet or bitter tastes. The aryl ureas are added to the foods, beverages or pharmaceutical compositions in amounts effective to inhibit the desired amount of sweetness or bitterness in the unmodified composition. Usually, this is from about 0.01 to about 10 percent by total weight of the composition and preferably 0.1-5 weight percent. The desired amount of aryl urea to be added in a given application is readily determined by one skilled in the art by conducting routine sensory experiments. All or a portion of the sweetness or bitterness can be inhibited by these aryl ureas. The present invention also includes physiologically acceptable salts of the aryl ureas which is their preferred form. Preferred salts include the alkaline earth metal salts of the aryl ureas, i.e., K, Na, Ca.

The present aryl ureas are compounds of the formula:

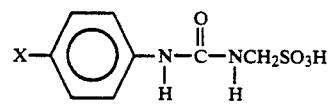

wherein
X represents
H,
CHO,
CN,
COC$_1$-C$_3$ alkyl,
CONH$_2$,
CONH(C$_1$-C$_3$ alkyl),
COO(C$_1$-C$_3$ alkyl),
COOH,
Br,
Cl,
F,
I or
NO$_2$, and
physiologically acceptable salts thereof.

Suitable physiologically acceptable salts include the alkaline earth metal salts as Na, K, Ca, Mg, The present aryl ureas are prepared by the well-known standard procedures used to prepare ureas. An aryl isocyanate in an organic solvent is treated with an alkaline salt of aminomethylsulfonic acid dissolved in water or a mixture of water and an organic solvent to afford the desired N-sulfomethyl-N'-aryl urea. This reaction is characterized as follows:

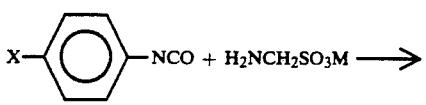

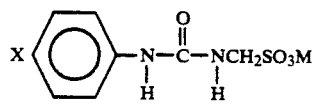

wherein M represents Na, K, Ca, Mg or the like.

The present reaction is conducted in an organic solvent such as acetonitrile, acetone, or ethyl acetate and water. The temperature and pressure at which this reaction is conducted is not critical but, preferably, ambient temperature and pressure conditions are employed. Once synthesized, the aryl ureas are recovered and purified employing well-known recovery and purification techniques. The aryl isocyanates are commercially available or can be prepared via standard known chemical procedures.

The present aryl ureas are added to foods, beverages and/or pharmaceutical preparations to inhibit or suppress the sweetness and/or bitterness of such compositions. Undesirably sweet products include sweet soft frozen confections and infused vegetables where the high sugar levels (overly sweet) are necessary to provide the desirable soft, frozen or infusion properties of these food products. The present aryl ureas are added in amounts necessary to inhibit the desired amount of sweet taste. All or a portion of the sweet taste can be masked.

The present aryl ureas are added to products which contain undesirably bitter organic compounds such as pharmaceuticals in amounts necessary to inhibit the desired amount of bitterness. Usually the aryl ureas are added to foods, beverages or pharmaceuticals in amounts from about 0.01 to about 10 percent by weight of the formulated end food, beverage or pharmaceutical product and advantageously from about 0.1 to about 5 weight percent and preferably from about 0.2 to about 2 weight percent. The optimum concentration of aryl urea in any given application is readily determined by one skilled in the art by conducting routine sensory experiments. The aryl ureas are incorporated into the food, beverage or pharmaceutical employing standard blending and mixing techniques. Mixtures of aryl ureas are also optionally employed. The present aryl areas inhibit the bitterness of organic compounds and surprisingly do not inhibit the bitterness of the inorganic chemical KCl.

The following examples illustrate the practice of the present invention, but should not limit its scope.

EXAMPLE 1

N-(Sodiosulfomethyl)-N'-(4-cyanophenyl)urea

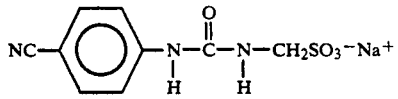

To a stirred solution of 4-cyanophenyl isocyanate (0.400 g, 2.78 mmol) in 5 mL of acetonitrile was added a solution of aminomethylsulfonic acid (0.308 g, 2.77 mmol) and sodium hydroxide (0.111 g, 2.78 mmol) in 1.5 mL of water. The reaction mixture was stirred for 4 days, then concentrated in vacuo. The residue was slurried in water, and filtered. The filtrate was concentrated in vacuo, slurried in acetonitrile and filtered to afford 0.67 g (99%) of crude product. The crude product was purified by recrystallization from ethanol/water to afford 0.423 g (62%) of the desired urea. Analytical results are given below.

$^1$H NMR (DMSO-D$_6$) δ9.37(s, 1H), 7.57(d, 2H, J=9.0 Hz), 7.52(d, 2H, J=9.0 Hz), 7.23(t, 1H, J=6.0 Hz), 3.99(d, 2H, J=6.0 Hz).

$^{13}$C NMR(DMSO-D$_6$) δ154.1, 145.0, 132.9, 119.5, 102.3, 64.9, 55.9.

M.P.>250° C.

IR(KBr)cm$^{-1}$ 3600(b), 3580, 2240, 1720, 1600, 1560, 1520, 1420, 1180, 1060.

Calcd. Anal. for C$_9$H$_8$N$_3$O$_4$S$_1$Na$_1$: C, 38.99; H, 2.91; N, 15.16. Found: C, 38.93; H, 2.86; N, 15.09.

EXAMPLE 2

N-(Sodiosulfomethyl)-N'-(4-nitrophenyl)urea

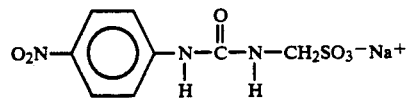

To a stirred solution (trace of solid present) of 4-cyanophenyl isocyanate (8.20 g, 50.0 mmoL) in 150 mL of acetonitrile was added a solution of aminomethyl sulfonic acid (5.56 g, 50.0 mmoL) and sodium hydroxide (2.00 g, 50.0 mmol) in 50 mL of water. The reaction mixture was stirred for 3.5 hours and then partially concentrated to remove the acetonitrile. The reaction slurry was diluted with 400 mL of water, stirred for 0.5 hours and filtered. The filtrate was concentrated and the residue slurried in 200 mL of acetonitrile. The slurry was filtered and the solid washed with acetonitrile and dried to afford 9.2 g of crude product.

The crude product was recrystallized from water to yield 6.76 g (45%) of the desired urea. Analytical results are given below.

$^1$H NMR (DMSO-D$_6$) Δ9.63(s, 1H), 7.98(d, 2H, J=9.1 Hz), 7.55(d, 2H, J=9.1 Hz), 7.51(m, 1H), 4.65(d, 2H, J=6.0 Hz).

$^{13}$C NMR (DMSO-D$_6$) Δ154.0, 147.2, 140.3, 140.3, 124.7, 117.0, 55.9.

EXAMPLE 3

N-(Sodiosulfomethyl)-N'-(4-carbamoylphenyl)urea

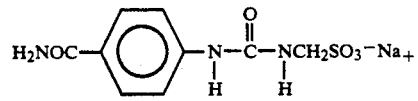

Hydrogen peroxide (30%, 3.9 mL, 34.2 mmol) was added to a stirred suspension of N-(Sodiosulfomethyl)-N'-(4-cyanophenyl) urea. (3.0 g, 10.83 mmol) in ethanol (7.5 mL), water (7.5 mL), and sodium hydroxide (6N, 2.38 mL, 14.01 mmol). The reaction mixture was stirred for 1 hour at room temperature. Stirring became difficult after 15 min and 10 mL of water was added at this point. Sodium bisulfite (2 g) was added to the reaction mixture to destroy excess hydrogen peroxide. The reaction mixture was then filtered, washed with cold water (5 mL) and dried to afford 2.90 g of the desired sodium salt of the urea. This crude product was recrystallized in hot water to afford 2.5 g (78%) of the pure desired material. $^1$H NMR (DMSO-D$_6$) Δ3.99 (d, 2H, J-5.9 Hz), 7.02 (t, 1H, J=6.0 Hz), 7.13 (s, 1H), 7.44 & 7.73 (AB quartet, 4H, J=8.6 Hz), 7.9 (s, 1H), 9.1 (s, 1H). $^{13}$C NMR (DMSO-D$_6$) Δ56.4, 117.0, 126.9, 128.8, 143.8, 154.8, 168.2.

EXAMPLE 4

Sweetness Inhibition

The taste modifier made in Example 1 was dissolved in a sucrose solution of known concentration. Three concentrations of the inhibitor were used (2, 3, and 4 mg/mL of solution). These three solutions and a sucrose solution containing no inhibitor were evaluated by each judge during each panel session. The solutions were presented in a random order and the results of each panel session were replicated three times. Sucrose references were tasted prior to each panel session (2%, 5%, 7.5%, 10%, 15% sucrose). These references were used to rate each sample.

The results of an inhibitor study are shown below. The inhibitor used in this set of experiments was the sodium salt of N-(sulfomethyl)-N'-(4-cyano-phenyl) urea.

| Con. of Inhibitor Used | Weight % of Sucrose Used | Weight % of Sucrose Perceived | Weight % of Sucrose Used | Weight % of Sucrose Perceived |
|---|---|---|---|---|
| 0.0 mg/mL | 5.6 | 6.0 | 7.5 | 8.5 |
| 2.0 mg/mL | 5.6 | 3.6 | 7.5 | 4.9 |
| 3.0 mg/mL | 5.6 | 2.1 | 7.5 | 4.2 |
| 4.0 mg/mL | 5.6 | 1.3 | 7.5 | 3.3 |

In similar embodiments, various compounds of Formula I and mixtures of those compounds are added to sweet tasting foods, beverages and pharmaceutical compositions to inhibit the sweet taste.

EXAMPLE 5

Bitterness Inhibition

The taste modifier made in Example 1 was dissolved in a caffeine solution of known concentration. Two concentrations of the inhibitor (3 and 4 mg/mL of solution) were used. These two solutions and a third solution containing only caffeine were evaluated by each judge during each panel session. The solutions were presented in a random order. Caffeine references (0.05%, 0.08% and 0.11%) were tasted prior to each panel session.

| Conc. of Inhibitor Used | Weight % of Caffeine Used | Weight % of Caffeine Perceived |
|---|---|---|
| 0.0 mg/mL | 0.11 | 0.11 |
| 3.0 mg/mL | 0.11 | 0.07 |
| 4.0 mg/mL | 0.11 | 0.05 |

In similar embodiments, various compounds of Formula I and mixtures of those compounds are added to bitter tasting foods, beverages and pharmaceutical compositions to inhibit bitter tasting organic compounds present therein.

We claim:

1. A compound of the formula

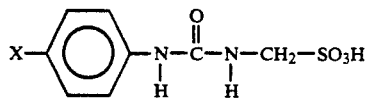

wherein
X represents
H,
CHO,
CN,
$CO_2C_1$-$C_3$ alkyl,
$COC_1$-$C_3$ alkyl,
$CONH_2$,
Br,
Cl,
F,
I,
$NO_2$
or a physiologically acceptable salt thereof.

2. The compound of claim 1 wherein X represents CN, CHO, $NO_2$ or $CONH_2$.

3. The compound of claim 1 wherein X represents CN (cyano).

4. The compound of claim 1 which is the sodium or calcium salt.